United States Patent
Swanstrom et al.

(10) Patent No.: US 6,669,707 B1
(45) Date of Patent: *Dec. 30, 2003

(54) METHOD AND APPARATUS FOR ATTACHING OR LOCKING AN IMPLANT TO AN ANATOMIC VESSEL OR HOLLOW ORGAN WALL

(76) Inventors: Lee L. Swanstrom, 1405 NW. 24th St., Portland, OR (US) 97210; Pedro Morales, Fronhofstrasse 26, 78532 Tuhlingen (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/489,820

(22) Filed: Jan. 24, 2000

Related U.S. Application Data

(63) Continuation of application No. 09/340,751, filed on Jun. 28, 1999, which is a continuation-in-part of application No. 09/120,161, filed on Jul. 21, 1998.

(51) Int. Cl.[7] .............................................. A61B 17/08
(52) U.S. Cl. ..................... 606/153; 606/151; 606/213; 623/1.11
(58) Field of Search ............................... 606/151, 153, 606/213, 216, 217, 72, 74, 103, 219, 220, 75, 232; 411/340, 483, 485, 501, 502, 513, 515; 24/72.7, 673, 706.11, 67.9, 67 P; 623/1.11, 1.23, 1.36; 16/93 D; 132/57.1, 284

(56) References Cited

U.S. PATENT DOCUMENTS

| | | | | |
|---|---|---|---|---|
| 327,974 A | * | 10/1885 | Truran | 411/483 |
| 357,813 A | * | 2/1887 | Brown | 411/513 |
| 793,123 A | * | 6/1905 | Carroll | 411/483 |
| 1,217,944 A | * | 3/1917 | Howell | 24/72.7 |
| 1,525,408 A | * | 2/1925 | Miller et al. | 411/513 |
| 2,645,833 A | * | 7/1953 | Wistedt | 24/72.7 |
| 2,983,974 A | * | 5/1961 | Tebb et al. | 411/483 |
| 3,154,825 A | * | 11/1964 | Edelberg et al. | 411/483 |
| 4,669,473 A | | 6/1987 | Richards et al. | |
| 4,705,040 A | | 11/1987 | Mueller et al. | |
| 4,926,858 A | | 5/1990 | Gifford, III | |
| 5,067,957 A | | 11/1991 | Jervis | |
| 5,207,695 A | | 5/1993 | Trout, III | |
| 5,275,611 A | | 1/1994 | Behl | |
| 5,342,393 A | | 8/1994 | Stack | |
| 5,350,399 A | | 9/1994 | Erlebacher | |
| 5,383,896 A | | 1/1995 | Gershony et al. | |
| RE34,866 E | | 2/1995 | Kensey et al. | |

(List continued on next page.)

FOREIGN PATENT DOCUMENTS

| | | |
|---|---|---|
| EP | 0 263 427 | 9/1987 |
| EP | 0 847 727 | 6/1998 |
| WO | WO 90/15582 | 12/1990 |
| WO | WO 97/09008 | 3/1997 |

*Primary Examiner*—Julian W. Woo

(57) ABSTRACT

An attachment or locking apparatus which can effectively secure an implant, such as a stent or stent graft, to a vessel or hollow organ wall and which allows minimally-invasive techniques, such as laparoscopy, to be used to attach the implant. The locking element is inserted through an anatomic vessel or hollow organ wall and the implant from outside of the vessel or hollow organ. The locking element preferably is composed of a thin retaining element and a clamping element at one end of the retaining element. A positioning device with an attached locking element may be inserted into the patient's body, such that the positioning device penetrates both the vascular or hollow organ wall and the implant deployed within the vascular or hollow organ wall. The clamping element, held within the positioning device, is then ejected into the vessel or hollow organ. The locking element is pulled tight, and then the locking element is secured into place. The locking element made be secured in place by physically deforming a portion of the retaining element outside of the vascular or hollow organ wall, by either winding or bending the retaining element.

21 Claims, 8 Drawing Sheets

U.S. PATENT DOCUMENTS

| | | |
|---|---|---|
| 5,474,573 A | 12/1995 | Hatcher |
| 5,500,000 A | 3/1996 | Feagin et al. |
| 5,527,355 A | 6/1996 | Ahn |
| 5,538,735 A | 7/1996 | Ahn |
| 5,593,422 A | 1/1997 | Muijs Van de Moer et al. |
| 5,624,669 A | 4/1997 | Leung et al. |
| 5,690,674 A | 11/1997 | Diaz |
| 5,700,277 A | 12/1997 | Nash et al. |
| 5,707,378 A | 1/1998 | Ahn et al. |
| 5,707,393 A | 1/1998 | Kensey et al. |
| 5,843,170 A | 12/1998 | Ahn |
| 6,248,116 B1 | 6/2001 | Chevillon et al. |

* cited by examiner

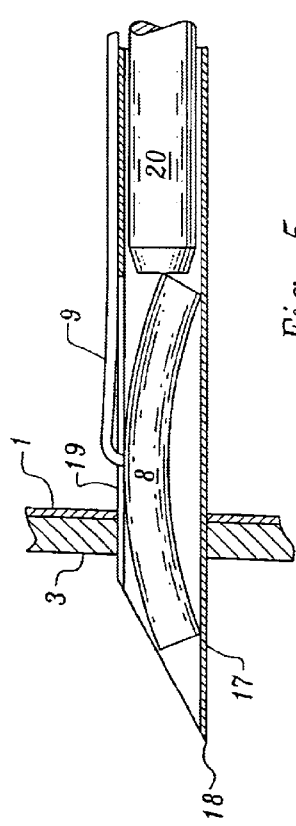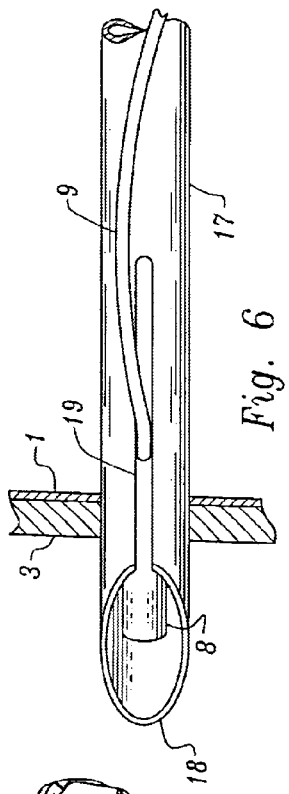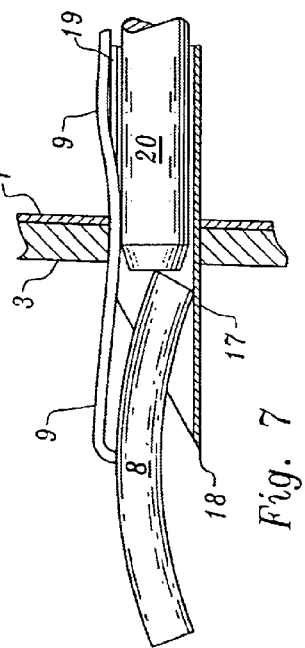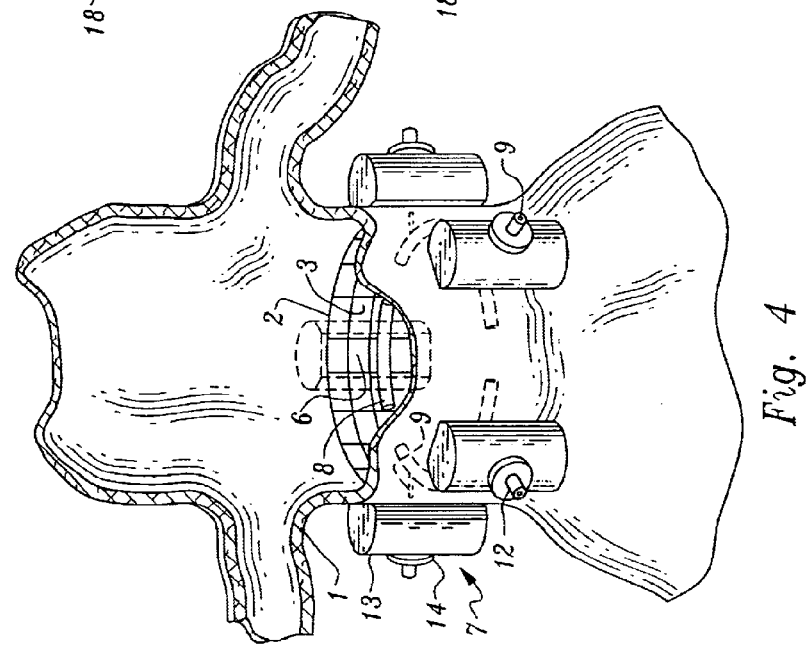

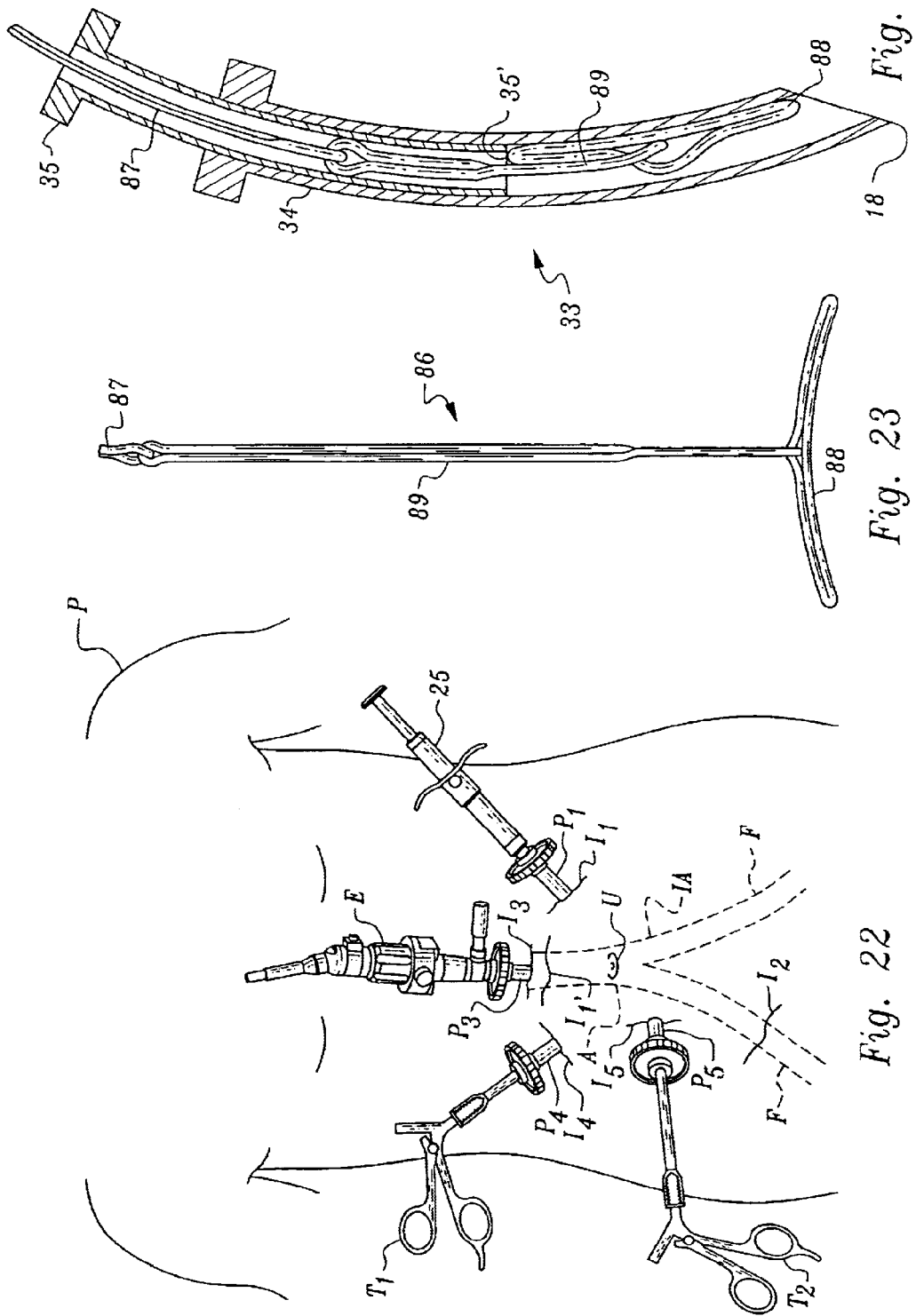

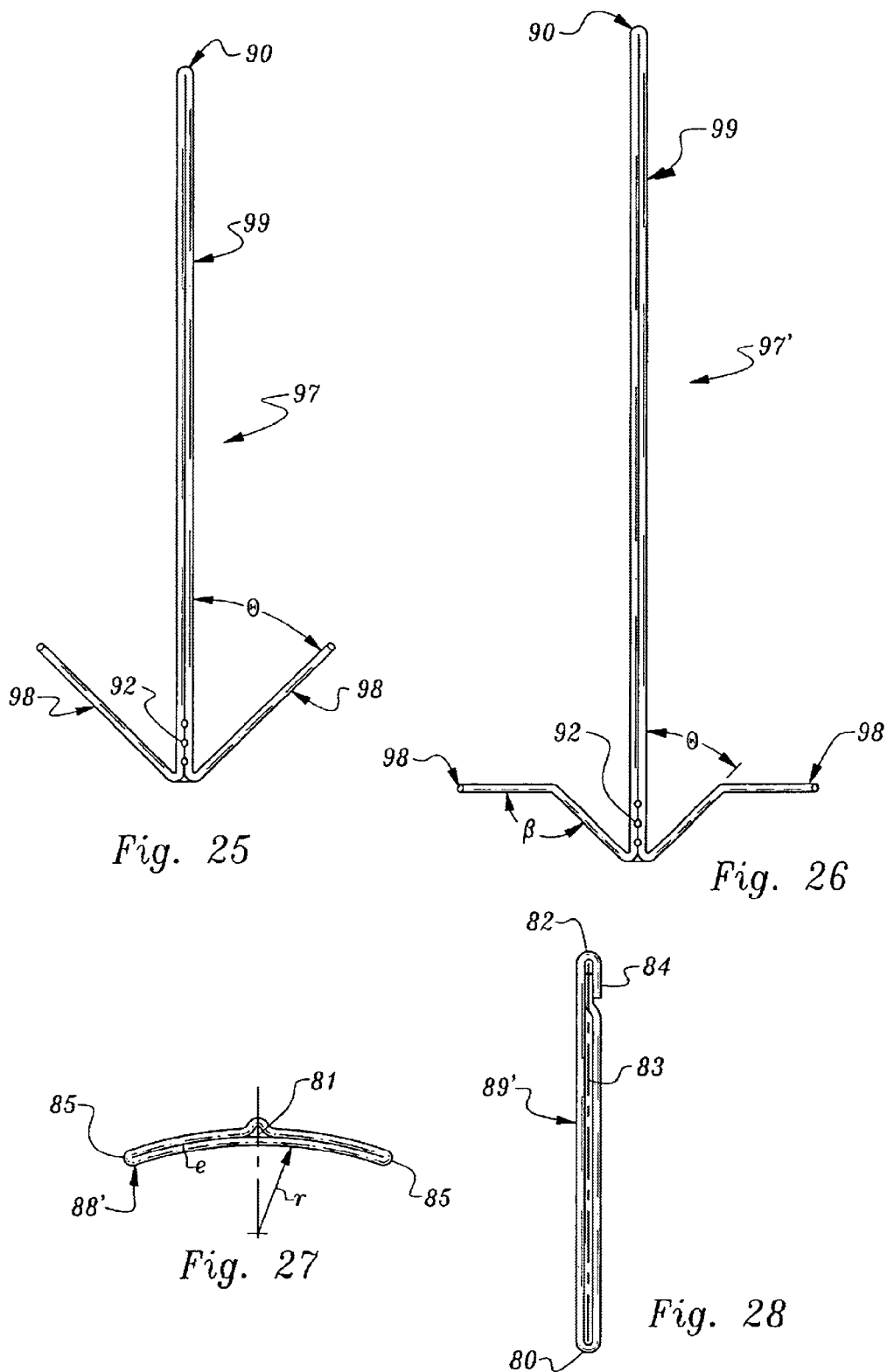

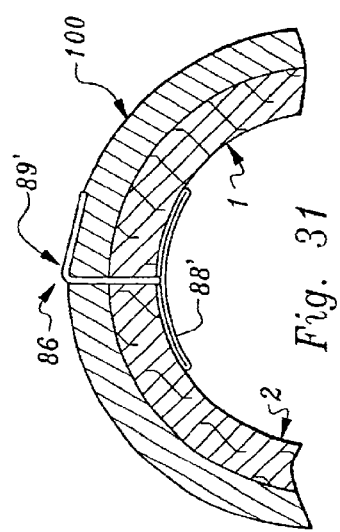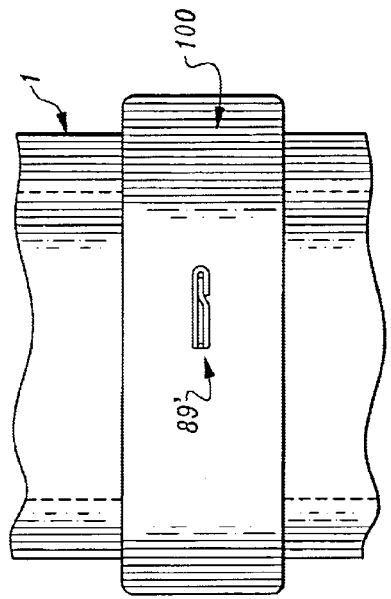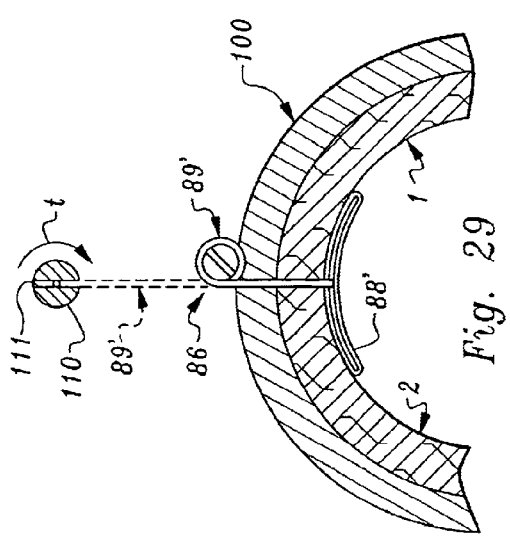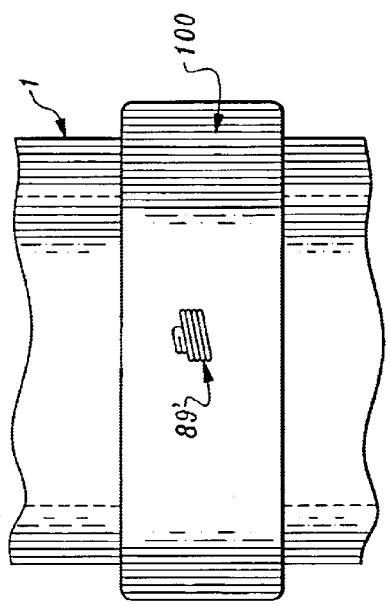

METHOD AND APPARATUS FOR ATTACHING OR LOCKING AN IMPLANT TO AN ANATOMIC VESSEL OR HOLLOW ORGAN WALL

This application is a continuation of U.S. patent application Ser. No. 09/340,751, filed Jun. 28, 1999 which is a continuation-in-part of U.S. patent application Ser. No. 09/120,161, filed Jul. 21, 1998.

BACKGROUND OF THE INVENTION

1. Field of the Invention

The present invention relates to an apparatus and a method for repairing an anatomic vessel wall or the wall of a hollow organ, such as the esophagus, particularly in the human body. In particular, the present invention relates to an attaching or locking element for attaching an implant, such as stent or stent graft, to a vascular or hollow organ wall from the outside of the wall as well as an instrument for positioning and inserting the attaching or locking element into the body. The present invention also encompasses a method for attaching or locking an implant to a vessel or hollow organ wall.

2. Description of the Related Art

An Abdominal Aortic Aneurysm ("AAA") is a weakening of the wall of the aorta in the abdominal area. AAAs pose a significant health problem and over 160,000 AAAs are diagnosed annually in the United States. A full 25% of AAAs will go on to eventually rupture; in spite of numerous advances in acute medical care, medical transport and resuscitation, ruptured AAAs continue to have a 50% mortality rate.

FIG. 1 shows an infrarenal AAA A' located in the torso T of a patient P, below the heart H and kidneys K and above the point of bifurcation B of the aorta A into the iliac arteries IA. As may be seen by comparing FIGS. 2 and 3, a normal aorta A (FIG. 2) exhibits non-bulging walls above the point of bifurcation B, while an aorta A which includes an AAA A' (FIG. 3) bulges outwardly from its normal condition. This bulging is the result of weakening of the aortic vessel walls.

The traditional surgical technique for treating AAAs involved excision of the aneurytic tissue and replacing that tissue with either a synthetic graft or a graft from another section of the patient's body. This approach required a large abdominal incision and total bowel displacement and large disruption of the retroperitoneum, followed by excision of the aneurytic tissue and attachment of the replacement graft to the vessel ends. Disadvantages of this prior art surgical technique include hypothermia, coagulation problems, prolonged ileus, a risk of sexual disfunction and significant pain and disfigurement. As a result of these significant disadvantages attendant to the traditional surgical technique, alternative techniques for AAA repair have been investigated and used.

In 1992, Juan Parodi, a surgeon, first described the placement of a percutaneous vascular prosthesis or stent in the abdominal aorta using interventional radiological techniques in *Transfemoral Intraluminal Graft Implantation for Abdominal Aortic Aneurvsms*, Ann. Vasc. Surg. 1991: 5:491–499. The prosthesis or stent effectively excluded, i.e., provided support for, the aneurysm sac, while avoiding a major access incision in the abdomen. This prior art technique required only a small groin incision, through which the stent was inserted and lead to the aneurysm site with appropriate stent guidance and deployment tools. Upon reaching the aneurysm site, the stent was deployed and grafted to the vascular walls of the aorta at the aneurysm site. A stent S deployed at an aneurysm A' is shown in dotted lines in FIG. 3. The use of stent grafts, as in this prior art technique, decreased patient morbidity, and because of the less invasive nature of the technique used to insert and deploy the graft, significantly reduced the problems with the traditional surgical technique for repairing AAAs.

Despite the advantages attendant the stent graft technique, difficulties in passing the stent to the aneurysm site, untimely opening of the stent, and complications, including emboli at the proximal and distal ends of the aneurysm, intimal damage, perforation, and thrombosis, have occurred. In addition, unsatisfactory methods and devices for proximal stent end fixation in order to prevent stent migration, as well as persistent endoleaks, have limited the effectiveness of stent grafts. The proximal stent end is the end of the stent nearest to the heart; this end needs to be fixed to the aorta in order to prevent the stent from migrating from its initial deployed position to a position where it does not fully exclude and support the AAA. This movement or migration can also cause endoleaks (L, FIG. 3), in which blood passes between the stent S and the aneurysm A', putting pressure on the aneurysm which can result in rupture.

When inserting implants, such as stents or stent grafts, into vessels or hollow organs, in particular when repairing an aneurysm using a stent graft, it is necessary that the stent introduced into the vessel or hollow organ be attached at both its distal and proximal ends tightly and permanently to the vessel wall surrounding the stent, in order to ensure that the stent does not migrate in the vessel and to ensure that the stent seals off the aneurysm, thus reinforcing the weakness in the vessel. Prior art stents used for repair of AAAs have used a variety of mechanisms for attaching the stent to the vessel wall. One mechanism used to attach a stent to a vessel wall is hook-shaped projections at the proximal and distal ends of the stent, which hook-shaped projections are pressed against the vascular wall from the inside of the vessel. The hook-shaped projections mechanically grip the vessel walls to secure the stent or stent graft to the vessel wall. In a similar attachment method, disclosed in U.S. Pat. No. 5,527,355, the stent or stent graft is secured in position against the vessel wall from the inside using hook-shaped retaining elements; these hook-shaped retaining elements are inserted into bands and surround the vessel externally.

PCT Publication No. WO 97/09008 to Medtronics shows a tubular implant used for repairing aneurysms. In this implant, a sealing layer is disposed at least at the ends of the implant, in order to reduce endoleaks. The implant described in this publication, however, does not include any mechanism for securely fastening the implant to the vessel wall to prevent migration.

U.S. Pat. No. 5,342,393 to Richard Stack of Duke University shows a device for repairing a perforation in a vascular wall. The device of that patent is not disclosed for any use in securing implants into an anatomic vessel or hollow organ. Furthermore, the device of that patent uses a large-diameter catheter or sheath which is inserted through a large perforation in the vessel wall. This device is therefore not suitable for securing an implant to a vessel or hollow organ wall, where large perforations are to be avoided in deploying the implant.

U.S. Pat. No. 4,669,473 to Acufex Microsurgical describes a surgical fastener used for fastening two or more sections of tissue to one another. This fastener is not disclosed or used for fastening of any type of anatomic vessel or organ, in particular any type of hollow anatomic vessel or organ, and the thick bar-like head of that fastener is specifically designed to be embedded within the tissue to be fastened. The head of the fastener also includes at least one pointed end for embedding in tissue. Furthermore, the fastener of that device is not used to clamp two walls together, nor is that fastener used to attach an implant to a vessel or hollow organ.

SUMMARY OF THE INVENTION

Prior art methods for affixing an implant, such as a stent or stent graft, to a vessel or hollow organ wall have not always been reliable. In addition, many of these prior art methods could only be employed using open surgical techniques requiring large incisions. These prior art methods, and the apparatuses used with these methods, have not been amenable to less-invasive techniques.

An object of the present invention is to provide an attachment or locking apparatus which can effectively secure an implant, such as a stent or stent graft, to a vessel or hollow organ wall and which allows less invasive techniques, such as laparotomy with a markedly reduced incision, and minimally-invasive techniques, such as laparoscopy or endoscopy, to be used to attach the implant.

A further object of the invention is to provide a method and device for deploying an attachment or locking apparatus for securing an implant, such as a stent or stent graft, to a vessel or hollow organ wall which achieves minimal yet reliable penetration of the vessel or hollow organ wall, as well as a method or device for manipulating the attaching or locking apparatus in the body.

A still further object of the invention is to provide an attachment or locking apparatus and a method and device for deploying the apparatus for fixation of a stent graft to a the wall of the aorta in the repair of AAAs which prevents stent migration and persistent endoleaks.

These and other objects of the present invention are achieved using a locking element which is inserted through the vessel or hollow organ wall and the implant from the outside of the vessel or hollow organ wall. The stent lock of the present invention preferably includes a thin retaining element. The retaining element has a clamping element joined flexibly at one end of the retaining element. A fixing element is secured in position on the retaining element to secure or attach the implant in place.

In, for example, the attachment of a stent or stent graft to a vascular wall, a thin cannula may be inserted into the patient's body, such that the cannula penetrates both the vascular wall and the stent or stent graft inserted within the vascular wall. The retaining element may then be inserted through the cannula so that the end with the clamping element is deployed on the inside of the stent or stent graft, and the other end projects through the stent or stent graft and the vessel wall. When withdrawing the end of the retaining element opposite the clamping element from the vessel, the clamping element, because of the flexible connection to the retaining element, tilts into a position transverse to the insertion opening. As a result, the clamping element is positioned against the inner wall of the stent or stent graft, so that the clamping element abuts against the interior of the vessel and the implant. The fixing element, already placed upon the retaining element or attachable upon the retaining element, is pushed from the outside against the vascular wall. In this manner, the distal and proximal ends of the stent or stent graft are locked together with the vessel wall and the stent or stent graft and the vessel wall are held between the clamping element and the fixing element. The fixing element can be fixed in position on the clamping element, after providing the necessary tension in both the stent or stent graft and the retaining element, by crimping or deformation, for example, or by a snap fit.

It is particularly advantageous if the clamping element is connected to the retaining element in the mid-section of the clamping element, so that when the retaining element is withdrawn from the opening in the vessel or hollow organ wall, the clamping element is positioned on both sides of the opening in the vessel or hollow organ wall across an equal contact area of the implant.

The clamping element must be designed so that it is insertable through a very small opening in the vessel or hollow organ wall and deployable into the interior of the vessel or hollow organ, and so that in the interior thereof, it nevertheless lies over a sufficiently large area against the implant so that the clamping element is reliably prevented from being withdrawn again through the opening in the wall. This can be ensured, for example, by the manner in which the clamping element is introduced into the interior of the vessel or hollow organ. The clamping element may be folded, bent or rolled into an elongated shape and inserted into the vessel or hollow organ, and thereafter may open, flex or expand therein. In a particularly preferred specific embodiment the clamping element may be pin-shaped. Thus, it becomes possible to insert the clamping element in the longitudinal direction of the cannula, with a very small cross-sectional puncture area, into the interior of the vessel or hollow organ. Once in the vessel or hollow organ, the clamping element flexes or spreads out into a transverse position, in front of the insertion opening, and thus prevents the clamping element from pulling out of the insertion opening. It is advantageous if the clamping element flexes or expands out radially from the retaining element, in a plane transverse to the longitudinal direction of the retaining element, thus providing a suitable contact area for the clamping element against the implant. The clamping element and retaining element may be integrally formed, or the retaining element may be embedded into, or otherwise connected to, the clamping element.

In one preferred embodiment, the clamping element can be curved in its transverse direction, so that it adapts or fits to the curve or shape of the implant or vessel or hollow organ wall. The clamping element preferably has ends which are not sharp, and may be smooth, preventing the ends of the clamping element from piercing or penetrating the vessel or hollow organ wall, thereby preventing damage.

One particularly preferred specific embodiment provides for the retaining element and the clamping element to be formed in one integral piece. The flexible joining of these two parts is then effected, for example, by manufacturing the retaining element and the clamping element integrally from a suitable polymeric or metallic material.

In another specific embodiment, the clamping element is tubular, and the retaining element is formed by a suture or thread whose two ends are introduced from opposite sides into the tubular clamping element and emerge together from the clamping element through the opening in the vessel or hollow organ wall.

It is beneficial if the fixing element is a permanently compressible sleeve through which the retaining element is passed. Initially, this sleeve is freely movable or slidable on the length of the retaining element. The fixing element can be brought forward closely against the outside of the vessel or hollow organ wall so that the wall and the implant, such as a stent or stent graft, are sufficiently compressed between the clamping element and the fixing element. When this condition is reached, the sleeve is crimped or deformed and thus secured in position with respect to the clamping element. As an alternative, the fixing element may be made of a resilient material, and may be snapped into an appropriate position using beads or other protuberances along the length of the retaining element.

At an end of the retaining element opposite the clamping element, an enlargement can be provided which prevents the fixing element, when it is not yet secured in position, from sliding off the retaining element. This feature prevents the fixing element from dislodging from the retaining element during the insertion procedure.

In another preferred specific embodiment, a pressure element, having a pressure surface which is arranged approximately transverse to the longitudinal direction of the retaining element and approximately parallel to the clamping element, is supported on the retaining element between the vessel or hollow organ wall and the fixing element. The pressure element preferably is freely movable along the retaining element. In particular, this pressure element can be a disk or band having a center through which the retaining element is passed. This pressure element is held by the fixing element against the outside of the vessel or hollow organ wall, and ensures that the force holding the vessel or hollow organ and the implant together is introduced over a large surface area on the outside of the vessel or hollow organ.

In addition, between the pressure element and the vessel or hollow organ wall, a large-area pressure-distribution element can be supported on the retaining element in a manner that it is moveable during insertion. This pressure-distribution element further distributes the pressure against the vessel or hollow organ wall. It is advantageous if the pressure-distribution element is elastically compressible, so that it positions itself over a large surface area against the vessel or hollow organ wall, thus reducing pressure peaks on the wall. In one preferred embodiment, the pressure-distribution element can have the shape of a cylinder, and the retaining element may pass transversely through the pressure-distribution element.

The individual parts of the locking element are made of materials well tolerated by the body, in particular the retaining element, the clamping element, the fixing element, the pressure element and/or the pressure-distribution element can be made of a non-absorbable plastic material. In other embodiments, it is also possible for the retaining element, the fixing element and/or the pressure element to be made of titanium, or possibly of another metal alloy well tolerated by the body.

In another preferred specific embodiment of the invention, the pressure-distribution element can be made of a foam or a non-woven fabric, so that it is elastically compressible and positions itself gently against the outer surface of the vessel or hollow organ wall.

It is also the object of the invention to provide a positioning or insertion instrument for inserting and locking in place the locking element of the present invention. This objective is fulfilled according to the present invention by a positioning instrument that includes a hollow needle, trocar or cannula into which at least the clamping element of the locking element is insertable, and an ejector to push the locking element out of the hollow needle, trocar or cannula. This apparatus may be large enough to be manipulable outside the body, or may be made to be inserted within the body so as to manipulable using appropriate endoscopic tools. Using such a positioning instrument, the locking element is accommodated in the hollow needle, trocar or cannula which can be inserted into the patient percutaneously, via laparoscopic, laparotomic or endoscopic techniques, and thereafter through the vessel or hollow organ wall and the implant. The clamping element is then pushed out of the hollow needle, trocar or cannula by an ejector. The ejector can extend out of the body cavity, to be actuated by hand by the surgeon, or could be located within the abdominal cavity, to be actuated using suitable endoscopic tools. After withdrawing the hollow needle, trocar or cannula from the vessel or hollow organ, the small opening caused by the hollow needle, trocar closes elastically around the retaining element which projects outwardly through the closed opening. The clamping element may be pressed against the inner wall of the implant by pulling on an opposite end of the retaining element. Thereafter, the pressure-distribution and/or pressure elements may be pressed against the outside of the vessel or hollow organ wall, and then the fixing element secured in place to lock the implant in place.

It is beneficial if the hollow needle, trocar or cannula is beveled at the end inserted into the patient, thereby tapering to a sharp point. It is also advantageous if the hollow needle, trocar or cannula has an elongated slot open toward the end inserted into the patient for receiving the clamping element. This is especially beneficial when the clamping element flexes or expands radially from the retaining element and therefore would be impeded by the inner wall of the hollow needle, trocar.

Depending on the location at which the hollow needle, trocar or cannula is to be inserted into the patient, the hollow needle, trocar or cannula can be optionally straight or curved. The hollow needle, trocar or cannula is preferably very thin, sharp and rigid, so that it may readily penetrate calcified vessel tissue, without creating a large puncture subject to weakening or rupture.

In the method of the present invention, as exemplified by its use in the treatment of an AAA, a first percutaneous incision is made at a location near the aneurysm site. A second percutaneous incision is made preferably in the groin or pubic area, to gain access to a femoral or iliac artery or the distal end of the abdominal aorta. Using standard interventional techniques the stent or stent graft is guided to the aneurysm site and then deployed. Access is gained to the exterior of the aorta at the aneurysm site through the first incision. The first incision may be a laparotomy incision, followed by suitable procedures to gain open access to the aorta, or may be a small incision as part of a laparoscopic procedure in which additional small incisions are made to deploy additional instruments into the abdomen. In either case, the positioning device, with an attached locking element is inserted through the first incision, guided to the aneurysm site, and then the hollow needle, trocar or cannula punctures the outside wall of the aorta and is inserted within the interior of the aorta and the stent or stent graft. The clamping element is then ejected, using an ejector, into the interior of the aorta and stent or stent graft. The hollow needle, trocar is then withdrawn. The locking element is pulled tight, and pressure-distribution and/or pressure elements are then slid down the locking element toward the aorta wall. The fixing element is then slid against the pressure-distribution and/or pressure elements, and secured into place by crimping, deforming, or by a snap fit. The free end of the locking element may then be cut off near the fixing element. The process of inserting and securing the locking element may be repeated until a sufficient number of locking elements are in place to securely hold the stent or stent graft to the aorta wall.

On embodiment of the invention can be made of one or more pieces of wire. Using this embodiment, the locking element may be secured or clamped in place by physically deforming a portion of the retaining element outside of the anatomic vessel or hollow organ wall. The physical deformation of the retaining element may be by winding or by bending. Embodiments of the locking element secured by this technique can be made from a single, bent, piece of wire or thread (which may also be welded in places), or may be made from two flattened loops of wire or thread.

BRIEF DESCRIPTION OF THE DRAWINGS

The following description of preferred specific embodiments of the invention, in conjunction with the drawings, serves to explain preferred embodiments of the invention more precisely.

FIG. 4 is a perspective view of a vessel with a number of applied locking elements.

FIG. 5 is a longitudinal cross-sectional view through the hollow needle or cannula of a positioning instrument with an undeployed inserted locking element.

FIG. 6 shows a plan view of the hollow needle or cannula of the positioning instrument of FIG. 5.

FIG. 7 shows a view similar to FIG. 5, with the ejector pushed forward and the clamping element partially pushed out.

FIG. 22 shows a plan view of a patient's body, demonstrating the manner in which the method of the present invention is implemented in the treatment of an AAA and some of the surgical tools used.

FIG. 23 shows a plan view of an eleventh embodiment of a locking element.

FIG. 24 shows an elevation, partially cross-section, view of the locking element of FIG. 23 used with the insertion tool of FIG. 10.

FIG. 25 shows a plan view of a twelfth embodiment of a locking element.

FIG. 26 shows a plan view of a thirteenth embodiment of a locking element.

FIG. 27 shows a plan view of an embodiment of a clamping element.

FIG. 28 shows a plan view of an embodiment of a retaining element.

FIG. 29 shows a cross-sectional view of an anatomic vessel or hollow organ wall with a locking element in place, using an embodiment of a securing technique.

FIG. 30 shows a side view of the anatomic vessel or hollow organ wall of FIG. 29.

FIG. 31 shows a cross-sectional view of an anatomic vessel or hollow organ wall with a locking element in place, using another embodiment of a securing technique.

FIG. 32 shows a side view of the anatomic vessel or hollow organ wall of FIG. 31.

DESCRIPTION OF THE PREFERRED EMBODIMENTS

FIG. 4 shows an anatomic vessel, in this case a section of the aorta, having a wall 1 into which a tubular implant 2 is inserted, so that implant wall 3 is in contact with vascular wall 1. In one embodiment of the present invention, the tubular implant 2 may be a stent or stent graft for repairing an Abdominal Aortic Aneurysm ("AAA"). In the exemplary embodiment shown in FIG. 4, a suitable known interventional tool such as a catheter is used to guide and deploy the tubular implant 2 using a minimally-invasive percutaneous incision. A free annular space 6 is formed in the interior of the vascular wall 1.

Figure 1:
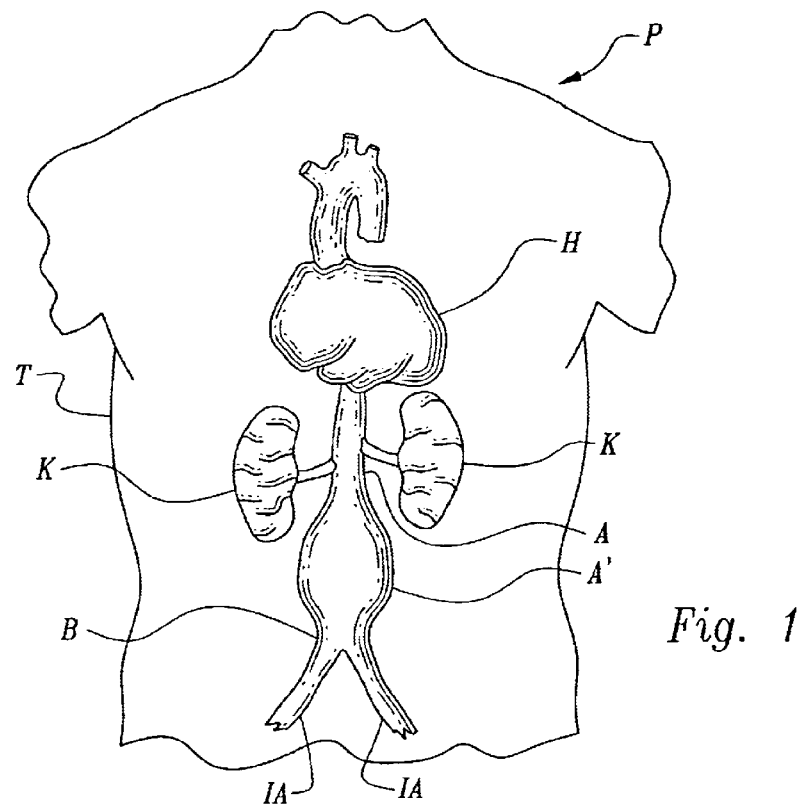
FIG. 1 is a view of an abdominal aortic aneurysm in a patient.
Figures 2, 3:
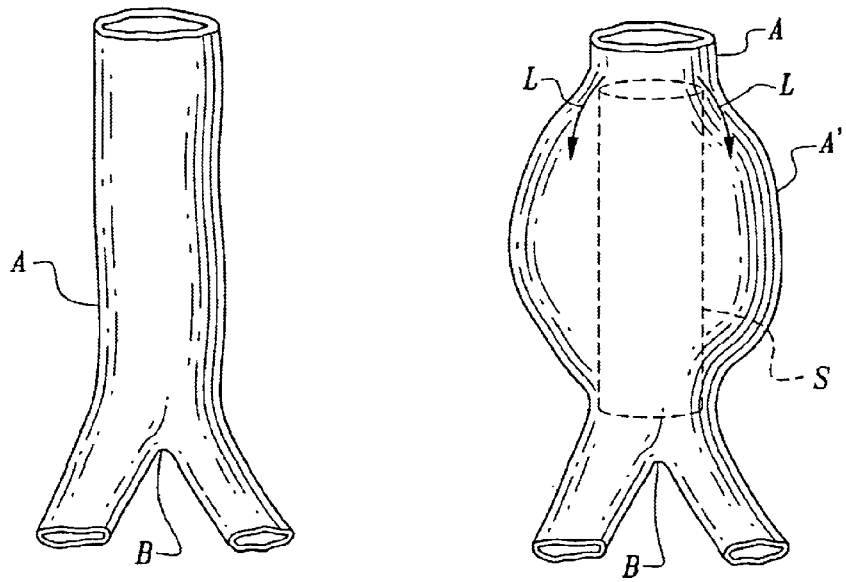
FIG. 2 is a detail view of an aorta without an abdominal aortic aneurysm.
FIG. 3 is a detail view of an aorta with an abdominal aortic aneurysm and an implant.
Figure 8:
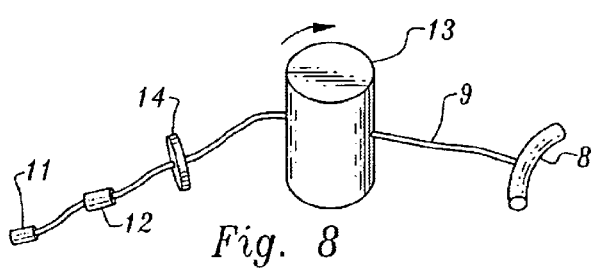
FIG. 8 shows a first embodiment of a locking element.

Vascular wall 1 and implant wall 3—lying flat against the vascular wall 1—are locked together by one or more locking elements 7. The locking elements 7 include a clamping element 8, which in a preferred embodiment may be pin-shaped, a thin retaining element 9 joined to the clamping element 8, and an enlargement 11 (FIG. 8) provided at a free end 10 of retaining element 9. It is possible, for example, to form the enlargement 11 using a sleeve slid onto free end 10 and pressed or crimped down at the free end 10, or the enlargement 11 may be molded, knotted or otherwise formed integrally with free end 10. The enlargement should be larger than an opening in the fixing element 12, to prevent the fixing element from sliding off of the free end 10. A fixing element 12, that may be in the form of a sleeve and have an opening through which the retaining element 9 passes, surrounds retaining element 9 and is initially freely moveable or slidable on the retaining element 9. The fixing element 12 may be captured between the clamping element 8 and the enlargement 11. The fixing element 12 may preferably be made of a deformable polymeric material which retains a deformed condition upon deformation or crimping, for example UHMWPE (Ultra High Molecular Weight Polyethylene). The fixing element 12 may alternatively be formed of a resilient material which allows the fixing element 12 to be snap fit over beads or protuberances on the retaining element 9. In each of the embodiments of the clamping elements described below the ends of the clamping element are preferably not sharp and may be smooth, so as to prevent ruptures or punctures of the implant 2 or vessel wall 1.

Between the clamping element 8 and fixing element 12, the retaining element 9 is passed transversely through a pressure-distribution element 13, which in a preferred embodiment may be cylindrical, and also through a central opening in a pressure element 14, which in a preferred embodiment may be in the form of a flat, circular disk or a band. Both the pressure-distribution element 13 and the pressure element 14 may be freely movable or slidable on retaining element 9.

Clamping element 8 is very thin so that it may be inserted into the vessel from the outside with minimal puncturing of the vessel; for example, the clamping element 8 may have a diameter of approximately 0.01–1 mm. The length of clamping element 8 is preferably only a fraction of the circumference of the vessel into which the locking element 7 is inserted, but should be long enough so that it is not pulled out of the vessel once inserted; for example the length of the clamping element may be approximately 8–20 mm. The clamping element 8 may be made of titanium or a titanium allow such as TIAL6V4, of any other metal alloy well tolerated by the body, or of a plastic material, in particular a non-absorbable plastic such as SURGILENE 2/0 USP™ polypropylene, manufactured by B. Braun, or a woven polyester, and may be in the form of either a polyfilament or a monofilament.

In the exemplary embodiment shown in FIG. 4, retaining element 9 is embedded into clamping element 8 and emerges radially from the clamping element 8 at its lengthwise center. Retaining element 9 may be secured to clamping element 8 by any known securing technique such as molding or deformation.

Retaining element 9 is preferably thin or thread-like, flexible and has a very small diameter. The retaining element 9 is preferably made of a non-absorbable polymeric material, such as SURGILENE 2/0 USP™ polypropylene, manufactured by B. Braun, and may be fashioned from a surgical suture material, and may be of a diameter approximately that of conventional suture materials. The elements that are freely movable on the retaining element 9—fixing element 12, pressure-distribution element 13 and pressure element 14—are safeguarded from being unintentionally pushed off the retaining element 9 by the enlargement 11 at free end 10 of the retaining element 9, which enlargement is larger than the opening in the fixing element 12, pressure-distribution element 13 and pressure element 14 through which the retaining element 9 passes. As a result, the locking element 7 forms a unitary structure which may be inserted into the body without the risk of individual parts becoming dislodged.

The retaining element 9 is preferably made of a material well tolerated by the body such as a metal wire or a plastic thread; in particular, the retaining element 9 can be made of non-absorbable plastic such as SURGILENE 2/0 USP™ polypropylene, manufactured by B. Braun. The retaining element 9 may also be formed integrally with, and of the same material as, retaining element 8, if desired.

The pressure-distribution element 13 may be elastically compressible and can be made, for example, of a non-woven fabric or a foam such as PTFE (polytetrafluoroethylene) fleece; this element can also be manufactured from a non-absorbable plastic material.

To join vascular wall 1 and implant wall 3, it is preferable that a number of locking elements 7 are arranged on the vessel along its periphery; preferably, the locking elements 7 are approximately equally spaced circumferentially around the vessel periphery. The locking element 7 may be attached at the proximal end of the implant 2, the distal end, or both ends. The locking elements 7 are preferably attached to the vessel using a positioning instrument as is shown in FIGS. 5–7, 10, 11, 11a–11c, 21 and 22.

As shown in FIGS. 5–7, a preferred embodiment of the positioning instrument of the present invention includes a hollow needle or cannula 17 having a beveled tip 18, and has, in a side wall, an axial slot 19 open toward the free end of the hollow needle or cannula 17. The hollow needle or cannula 17 should be of a relatively small outer diameter, for example 0.25–1.0 mm, and should be fashioned of a relatively strong material so that it may easily penetrate a vessel wall 1 which may be calcified. The beveled tip 18 should also be very sharp, so as to more readily penetrate the vessel wall 1 and the implant 2. An ejector 20 is supported in a manner so that it is longitudinally movable in the interior of hollow needle or cannula 17. Ejector 20 can be pulled back so that a clamping element 8 can be completely inserted into hollow needle or cannula 17 in front of ejector 20, as shown in FIG. 5. In this inserted state, retaining element 9 enters longitudinal slot 19 and is then arranged on the outer side of hollow needle or cannula 17. The retaining element 9 could alternatively be retained within hollow needle or cannula 17, between the hollow needle or cannula 17 and the ejector 20.

In the state shown in FIG. 5, hollow needle or cannula 17 can be inserted from the outside of the vessel—using laparoscopic, endoscopic or open surgical techniques described in pertinent detail below—through vascular wall 1 and implant wall 3, into the vessel, tip 18 then arriving in annular space 6. As soon as the clamping element 8 is completely within the annular space 6, ejector 20 may be pushed forward so that clamping element 8 is pushed out of hollow needle or cannula 17 (FIG. 7) and is now free in annular space 6. Hollow needle or cannula 17 is subsequently withdrawn from the vessel, and the opening formed by said hollow needle or cannula 17 is closed by the elasticity of vascular wall 1 and implant wall 3. However, retaining element 9 projects outwardly through this opening, and the vascular wall 1 and implant wall 3 close around the retaining element 9.

By pulling on the retaining element 9, the pin-shaped clamping element 8 flexes or expands to a position approximately transverse to the retaining element 9 and approximately parallel to the vascular wall 1 and implant wall 3, and becomes positioned against implant wall 3. The clamping element 8 thus is anchored against the inner side of implant 2. While continuing to keep retaining element 9 taut by pulling on the free end 10, the surgeon next pushes pressure-distribution element 13, pressure element 14 and fixing element 12 along the length of the retaining element 9 in the direction toward vascular wall 1, until the vascular wall 1 and implant wall 3 are clamped between clamping element 8 on one side and pressure-distribution element 13 and/or pressure element 14 on the other side, and thus are pressed flat against each other. In this state, fixing element 12 is slid down the retaining element 9 and then secured in position on retaining element 9, for example, by pressing or crimping the sleeve together using a suitable tool or instrument. Alternatively, the fixing element 12 can be snap fit in position. In this manner, a locking element 7 has been secured on the vessel which holds vascular wall 1 and implant wall 3 flat against one another, as shown in FIG. 4. The end of the retaining and locking element 9 passing beyond the fixing element 12 can then be cut off using a suitable tool or instrument.

Locking elements 7 of the present invention are placed in number in the circumferential direction around the vessel. In this manner, a number of fixing points are produced along the periphery, which lock implant wall 3 and vascular wall 1 permanently and imperviously together (FIG. 4).

Figure 9:
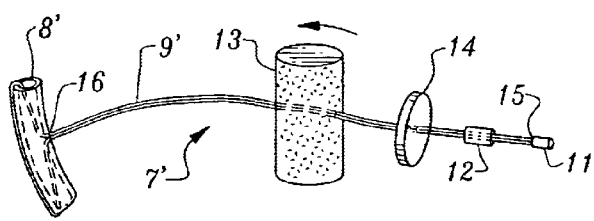
FIG. 9 shows a second embodiment of a locking element having a tubular clamping element.

A locking element 7' is shown in the exemplary embodiment of FIG. 9 which differs from that of FIGS. 4–8 only in that clamping element 8' is formed from a short hollow tube, preferably of titanium alloy such as TIAL6V4 or a nonabsorbable polymeric material. In the embodiment of FIG. 9, retaining element 9' is in the form of a loop; the free ends 15 of the retaining element 9' are introduced from opposite ends into tube-shaped clamping element 8' and emerge radially through an opening 16 in the lengthwise center wall area of the clamping element 8'. The short hollow tube of the clamping element 8' may be manufactured by laser-drilling a thin titanium alloy or polymeric rod or pin.

The clamping element of the present invention may preferably be manufactured to be of a slightly curved shape, or to flex or expand into a slightly curved shape after insertion into the vessel, so as to better conform with the curved inner wall 3 of the implant 2.

Figure 10:
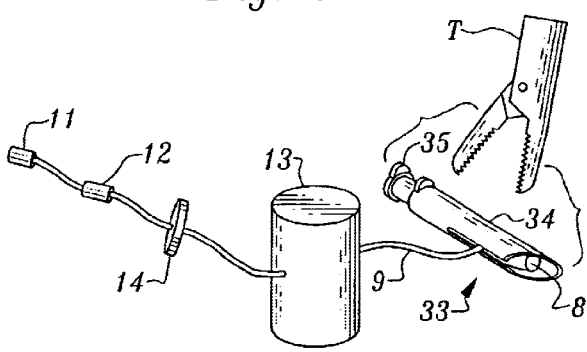
FIG. 10 shows the embodiment of FIG. 8 mounted in an intra-abdominal cannula and ejection tool manipulated by an endoscopic tool.

FIG. 10 shows a first embodiment of a positioning instrument 33 of the present invention, which is used intra-abdominally. The positioning instrument 33 includes a hollow needle or cannula portion 34 and an ejector portion 35. The ejector portion slides within the interior of cannula portion 34, so that in a retracted position (shown in FIG. 10), a clamping element 8 is inserted within the hollow needle or cannula portion 34, and in an ejected position (similar to the position show in FIG. 7), clamping element 8 is ejected from the hollow needle or cannula portion 34. The positioning instrument is of a size comparable to conventional intra-abdominal needles or cannulas used in endoscopic surgical techniques, and is inserted into the abdominal cavity, and manipulated within that cavity once inserted, by a suitable endoscopic grasping tool T or other endoscopic tools.

Figure 11A:
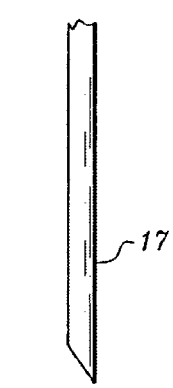
FIGS. 11a–11b show first, second and third embodiments of the cannula of the present invention.
Figures 11B, 11C:
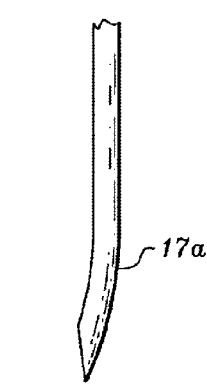
Figure 11:
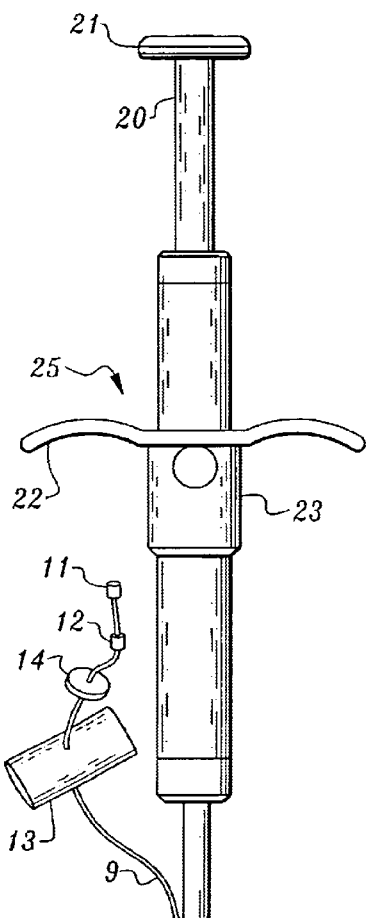
FIG. 11 shows a plan view of a positioning tool of the present invention, including a locking element.

FIG. 11 shows a view of a second embodiment of a positioning instrument 25 of the present invention. As discussed in detail above, the positioning instrument includes a hollow needle or cannula 17 having a beveled tip 18, and has, in a side wall, an axial slot 19 open toward the free end of the hollow needle or cannula 17. An ejector 20 is supported in a manner that it is longitudinally movable or slidable in the interior of hollow needle or cannula 17 and the interior of the instrument body 23, and can be pulled back so that a clamping element 8 can be completely inserted into hollow needle or cannula 17 in front of ejector 20. The ejector 20 may be made of a flexible material so that it can be accommodated in a curved hollow needle or cannula 17a, 17b (FIGS. 11b, 11c) and may include a knob or handle 21 at one end which allows the surgeon to eject the clamping element from the positioning instrument into the vessel. The instrument body 23 may include finger grips 22 to assist in ejecting the locking elements using the ejector 20.

FIGS. 12–18a show various alternative embodiments of the locking element of the present invention. It is to be understood that FIGS. 12–18a show only the retaining and clamping element portions of the locking elements, and that the other components of the locking elements are not shown for clarity.

Figure 12:
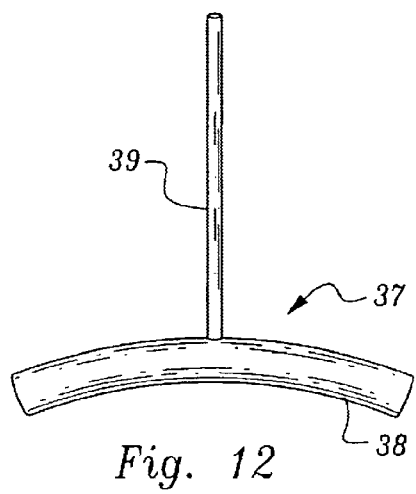
FIG. 12 shows a third embodiment of a locking element.
Figure 13:
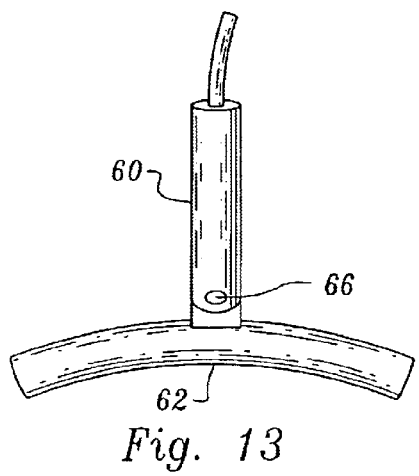
FIG. 13 shows a fourth embodiment of a locking element.
Figure 14:
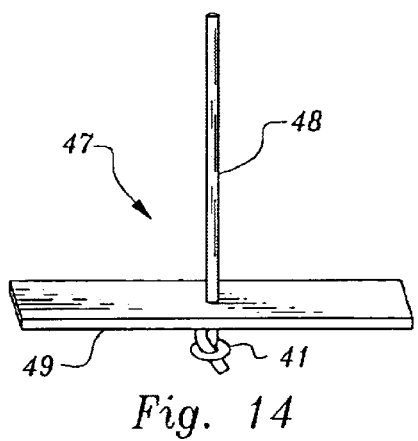
FIG. 14 shows a fifth embodiment of a locking element.
Figure 15:
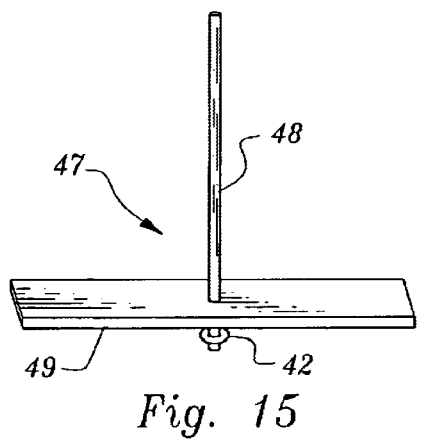
FIG. 15 shows a sixth embodiment of a locking element.

FIG. 12 shows an embodiment of the locking element 37 in which the retaining element 39 and the clamping element 38 are integrally molded or manufactured in an approximately "T" shape. This locking element 37 could be manufactured either of a metallic material or a polymeric material. In the embodiment of FIG. 13, the retaining element 60 is attached to the clamping element 62 through a hinge 66, which allows these two elements to pivot relative to one another. In the embodiment of the locking element 47 in FIG. 14, the retaining element 48 is a wire or thread with a knot 41 at one end. The clamping element 49 is formed by a flat spring of a metallic or polymeric material, which has a hole 42 through which the wire or thread of the retaining element 48 passes. The knot 41 prevents the spring of the clamping element 49 from dislodging from the retaining element 47. In a variation of the embodiment of FIG. 14 shown in FIG. 15, the knot 41 may be replaced by a protuberance or bead 42.

Figure 16:
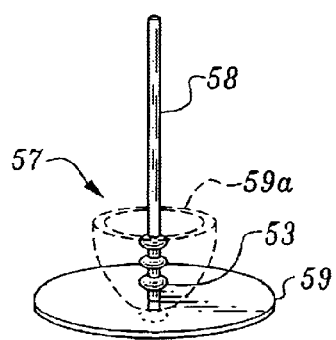
FIG. 16 shows an seventh embodiment of a locking element.

FIG. 16 shows an embodiment of a locking element 57 in which the clamping element 59 is disk-shaped in a flexed or expanded condition, and which assumes a conical or hemispherical configuration 59' when retained contracted or folded inside the hollow needle or cannula 17 for insertion into the vessel. The retaining element 58 may include a series of protuberances or beads 53 along its length. These beads 53 may be used to fix a fixing element 12 in place without deformation or crimping. The fixing element 12 would be slid down the length of the retaining element 58, snapping over the beads 53, until the fixing element 12 reaches a position in which it securely clamps the clamping element 59 against the implant wall 3. The bead 53 above the fixing element 12 would prevent that element from thereafter slipping back away from the vessel, thereby loosening the locking element 57. In this way, the fixing element 12 is secured by a snap connection or fit along the length of the retaining element 58.

Figure 17:
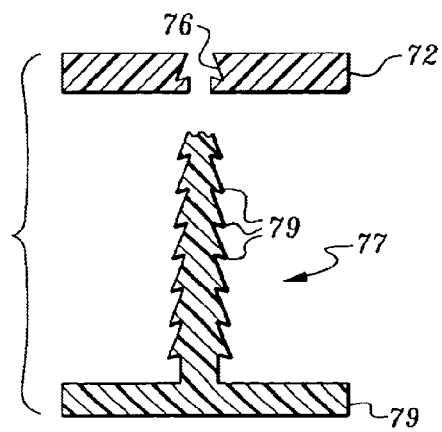
FIG. 17 shows an eighth embodiment of a locking element.

FIG. 17 shows an embodiment of a locking element 77 in which the clamping element 79 is integrally formed with the retaining element 78. The retaining element 78 includes teeth 79 along its length, which interact with teeth 76 on fixing element 72, allowing only one-way movement of fixing element 72 along retaining element 78. The fixing element 72 would be slid down the length of the retaining element 78, snapping over the teeth 79, until the fixing element 72 reaches a position in which it securely clamps the clamping element 79 against the implant wall 3. The interaction of teeth 79 and 76 would prevent fixing element 72 from thereafter slipping back away from the vessel, thereby loosening the locking element 77. In this way, the fixing element 72 is secured along the length of the retaining element 78.

Figure 18A:
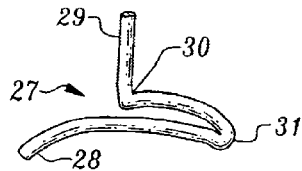
FIG. 18a shows a ninth embodiment of a locking element.
Figure 18B:
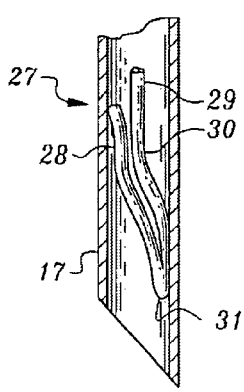
FIGS. 18b and 18c show the embodiment of FIG. 18a inserted in a cannula.
Figure 18C:
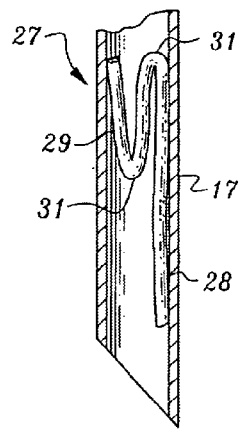

In FIGS. 18a–18b, the locking element 27 is formed of an integrally-manufactured wire or thread of a resilient or shape-memory material, which could either be metallic or polymeric. The retaining element 29 joins the clamping element 28 by way of a series of two bends or hinges 30, 31. As shown in FIG. 18a, the locking element 27 is manufactured to expand or flex into a shape in which the clamping element 28 is approximately perpendicular to the retaining element 27. During insertion through hollow needle or cannula 17 (FIGS. 18b and 18c), the locking element 27 may be deformed into one of two configurations, shown in FIGS. 18b and 18c, which allow insertion through hollow needle or cannula 17.

Figure 19:
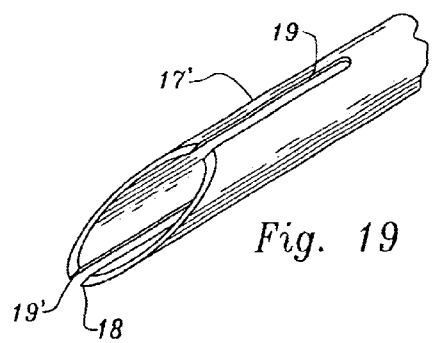
FIG. 19 shows a perspective view of a fourth embodiment of a hollow needle or cannula.
Figure 20:
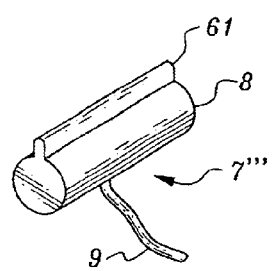
FIG. 20 shows a perspective view of a tenth embodiment of a locking element used with the hollow needle or cannula of FIG. 19.

FIGS. 19 and 20 show an alternative configuration of a hollow needle or cannula 17' and an alternative configuration of a locking element 7'" used with that hollow needle or cannula 17'. The hollow needle or cannula 17' of FIG. 19 differs from the hollow needle or cannula 17 of FIGS. 5–7 in that the hollow needle or cannula 17' of FIG. 19 include an additional slot 19' opposite the slot 19. The locking element 7''' includes, on the clamping element 8 a ridge 61, which ridge 61 fits into and slides along the additional slot 19'. The interaction between ridge 61 and additional slot 19' helps to guide the clamping element 8 into a proper position within the vessel.

Figure 21A:
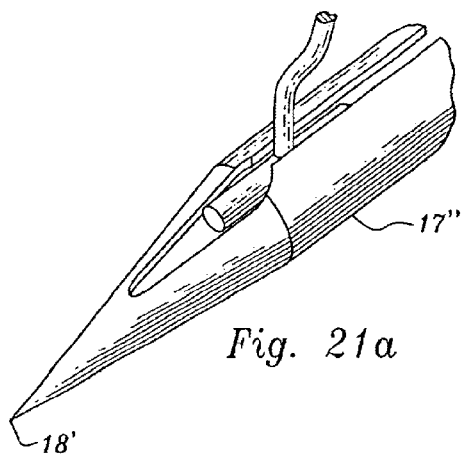
FIG. 21a and FIG. 21b show, respectively, perspective and elevation end views of a trocar of a positioning instrument with an undeployed inserted locking element.
Figure 21B:
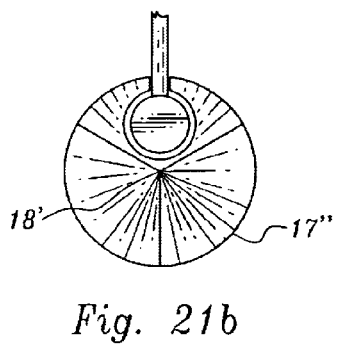

FIG. 21 is an illustration of an alternative insertion tool 17'', in which a trocar tip 18' is used instead of the hollow needle or cannula. In all other respects, however, the embodiment of FIG. 21 is identical to the embodiment of FIGS. 5–7. The trocar tip 18' can be used with either the embodiment of the insertion tool as shown in FIGS. 10 or 11.

FIG. 22 is an illustration of a patient P and the manner in which the method of the present invention is used to repair an AAA. A first percutaneous incision $I_1$, is made, at a location near the site of the AAA or the site where the implant 2 is to be retained. A second percutaneous incision $I_2$ is made, preferably in the groin or pubic area near one of the femoral arteries F or one of the iliac arteries IA. Alternatively, the second percutaneous incision $I_2$ could be made at the distal end of the abdominal aorta A, if the femoral arteries F or iliac arteries IA are too small or obstructed, and therefore inappropriate for the use of standard interventional techniques. Suitable interventional techniques known in the art, such as those described by Parodi, are used to transfer an implant through the incision $I_2$ and into the aorta A until the stent or stent graft is in position at the location of an AAA. Suitable known techniques can be used to properly position the implant. Thereafter as known in the art, the stent or stent graft is deployed or expanded so that the wall 3 of the implant 2 contacts the vascular wall 1. The positioning tool 25 is inserted through a port $P_1$, which has been positioned through first incision $I_1$, along with a locking element (of any of the above-described embodiments)—including one or more of the fixing element 12, pressure-distribution element 13 and pressure element 14 contained on the retaining element. Using an endoscope E inserted through a port $P_3$ which has been positioned through a third incision $I_3$, the positioning tool 25 is guided so that the hollow needle or cannula enters the vascular wall 1 at the location of an end of the stent or stent graft 2, and so that the hollow needle or cannula punctures and passes through both the vascular wall 1 and the stent or stent graft 2 (FIGS. 5–7). The ejector 20 is then pushed down the length of the hollow needle or cannula to thereby eject the clamping element within the vessel (FIG. 7). The hollow needle or cannula is then pulled out of the vessel, and the end of the retaining element (which preferably is held outside the patient's P body) is then pulled until it is tight, using, for example, grasping forceps or other suitable tools. Thereafter, the pressure-distribution element 13 and pressure element 14 may be slid down the retaining element until they are pressed against the outside of the vessel wall, and the fixing element 12 may then be slid down the retaining element and thereafter deformed, crimped or snapped in place. The pressure-distribution element 13 and pressure element 14 may be slid down the retaining element using suitable endoscopic suturing or grasping forceps or tools, and the fixing element 12 may be slid down the retaining element using similar tools. If it is desired to deform or crimp the fixing element 12 in place, a suitable endoscopic forceps may be used for this purpose. This procedure may be repeated as many times as necessary to put into place a number of locking elements needed to secure the stent or stent graft 2 in place. The ends of the retaining elements may thereafter be cut, at a position near the fixing element, using suitable endoscopic cutting tools. Suitable surgical tools $T_1$, $T_2$ may be deployed through ports $P_4$, $P_5$ in incisions $I_4$, $I_5$ and used as part of the procedure for securing the stent or stent graft in place. Such tools $T_1$, $T_2$ could include, but are not limited to, various clamps, graspers, forceps, scissors, needleholders, trocars, endoscalpels, dissecting spatulas, suction devices, rummels, containers or endracks.

FIG. 23 is an illustration of an additional embodiment of the locking element 86 of the present invention. The clamping element 88 is configured as a flattened loop of a metallic material, preferably Phynox™ wire of 0.2–0.3 mm diameter. Similarly, the retaining element 89 is configured as a flattened loop of a metallic material, preferably Phynox™ wire of 0.2–0.3 mm diameter. The two loops of clamping element 88 and retaining element 89 are interlinked, at one end of retaining element 89 and at the center of clamping element 88. At the other end of the retaining element 89, a loop of security thread or suture material 87 can pass through the loop of the retaining element 89.

FIG. 24 shows the embodiment of the locking element 86 of FIG. 23 used with the positioning instrument 33 of FIG. 10. As shown in FIG. 24, the clamping element 88 pivots relative to retaining element 89 to assume a elongated position when inserted in positioning instrument 33. This pivoting is a result of the interlinking of the loops of clamping element 88 and retaining element 89. Depression of ejector portion 35 toward beveled tip 18 causes a ejector end 35' to push clamping element 88 out of beveled tip 18, similar to the manner shown in FIGS. 5–7. Once the clamping element 88 has been ejected from the positioning instrument 33, the clamping element 88 pivots into a position transverse to the retaining element 89. It is to be understood that the locking element 86 could also be used with the positioning instrument 25 of FIG. 11.

FIG. 25 shows a further embodiment of a locking element 97 of the present invention. The locking element 97 of FIG. 25 is made of a single piece of wire or thread, which is bent or formed, and otherwise secured, into the configuration shown in FIG. 25. In a preferred embodiment of the invention of FIG. 25, the locking element 97 is made of a single piece of a metallic wire or thread, preferably Phynox™ wire of 0.2–0.3 mm diameter. The wire or thread is bent, using conventional bending techniques for wire or thread of that size, to form a retaining element 99 and a clamping element 98. The retaining element 99 in the embodiment of FIG. 25 is formed when the wire or thread is bent 360° at a center of the wire or thread, to thereby form a retaining element 99 end 90. The clamping element 98 is formed when the wire or thread is bent through an angle θ at each end. The angle θ is preferably on the order of 45°, in the embodiment of FIG. 25. In order to secure the wire or thread into the configuration shown in FIG. 25, one or more laser welds 92 may be made on the locking element 97. In the embodiment shown in FIG. 25, three laser welds 92 have been made on the retaining element 99, near the location of the bends forming the clamping element 98.

FIG. 26 shows a modified embodiment of the locking element shown in FIG. 25. In the embodiment of FIG. 26, the locking element 97' is made of a single piece of wire or thread, which is bent or formed, and otherwise secured, into the configuration shown in FIG. 26. In a preferred embodiment of the invention of FIG. 26, the locking element 97' is made of a single piece of a metallic wire or thread, preferably Phynox™ wire of 0.2–0.3 mm diameter. The wire or thread is bent, using conventional bending techniques for wire or thread of that size, to form a retaining element 99 and a clamping element 98'. The retaining element 99 in the embodiment of FIG. 26 is formed when the wire or thread is bent 360° at a center of the wire or thread, to thereby form a retaining element 99 end 90. The clamping element 98' is formed when the wire or thread is bent, first through an angle θ at each end, and then through an angle β at each end. The angle θπis preferably on the order of 45° and the angle β is preferably on the order of 135°, in the embodiment of FIG. 26. In order to secure the wire or thread into the configuration shown in FIG. 26, one or more laser welds 92 may be made on the locking element 97'. In the embodiment shown in FIG. 26, three laser welds 92 have been made on the retaining element 99, near the location of the bends forming the clamping element 98'.

FIGS. 27 and 28 show details of the components of a locking element 86' which is a variation on the locking element shown in FIG. 23. The clamping element 88' is configured as a flattened loop of a metallic material, preferably Phynox™ wire of 0.2–0.3 mm diameter. Similarly, the retaining element 89' is configured as a flattened loop of a metallic material, preferably Phynox™ wire of 0.2–0.3 mm diameter. The two loops of clamping element 88' and retaining element 89' are interlinked, at one end 80 of retaining element 89' and at the center 81 of clamping element 88'. The retaining element 89' is formed using a single piece of wire or thread, bending it 360° at two locations to form two ends 80, 82 such that a small gap or space 83 is formed. The ends of the wire or thread are preferably crimped over one another at a location 84, and could be laser welded at that location to secure the retaining element 89' in the configuration shown in FIG. 28. The clamping element 88' is formed in a manner similar to the retaining element 89'. The clamping element 88' is formed using a single piece of wire or thread, bending it 360° at two locations to form two ends 85. A bend is formed at the center 81 of the clamping element 88', thereby creating a small opening or space. The clamping element 88' is also preferably bent along a radius r, which may be on the order of 14.8 mm, to thereby form a curve in the clamping element 88'. The ends e of the wire or thread are preferably located closely adjacent one another, and could be laser welded at that location to secure the clamping element 88' in the configuration shown in FIG. 27.

FIGS. 29 and 30 show a securing technique which may be used with any of the embodiments of the locking element shown in FIGS. 23 and 25–28, although those figures show a locking element of the type shown in FIGS. 23 and 27–28. As described in detail above, a tubular implant 2, such as a stent or stent graft, is placed within the interior of an anatomic vessel or hollow organ wall 1. A reinforcement ring 100 may be placed around the circumference of the anatomic vessel or hollow organ wall 1, at one or both ends of the tubular implant 2. Thereafter, the locking element 86 is passed through the reinforcement ring 100, the anatomic vessel or hollow organ wall 1 and the tubular implant 2 so that the clamping element 88' is within the interior of the anatomic vessel or hollow organ wall 1. The locking element 86 is preferably passed through the reinforcement ring 100, the anatomic vessel or hollow organ wall 1 and the tubular implant 2 using a device of the type shown in FIGS. 5–7, 11, 19, 21 or 24, and in particular a hollow needle or trocar device with a sharp tip, which readily punches through reinforcement ring 100, the anatomic vessel or hollow organ wall 1 and the tubular implant 2. Once the clamping element 88' is located within the interior of the anatomic vessel or hollow organ wall 1 and the tubular implant 2, the retaining element 89' is pulled slightly outwardly, thereby seating the clamping element 88' against the tubular implant 2. Next, a tool 110 is used to physically deform the portion of the retaining element 89' outside the anatomic vessel or hollow organ wall by winding or wrapping into the condition shown in solid lines in FIGS. 29 and 30. The tool 110 preferably includes a cylindrical tip with a slot 111 passing through one end. The end 82 of the retaining element 89' is fitted within the slot 111. Thereafter, the tool 110 is rotated or twisted in the direction t, which results in the retaining element being wrapped or coiled until it contacts the reinforcement ring 100, as shown in solid lines in FIGS. 29 and 30. Thereafter, the tool 110 may be disengaged from the retaining element 89'. In this manner, the retaining element 89' is clamped against the reinforcement ring 100 and the clamping element 88' is clamped against the tubular implant 2, thereby clamping the tubular implant 2 to the anatomic vessel or hollow organ wall 1.

FIGS. 31 and 32 show an alternative securing technique which may be used with any of the embodiments of the locking element shown in FIGS. 23 and 25–28, although those figures show a locking element of the type shown in FIGS. 23 and 27–28. As described in detail above, a tubular implant 2, such as a stent or stent graft, is placed within the interior of an anatomic vessel or hollow organ wall 1. A reinforcement ring 100 may be placed around the circumference of the anatomic vessel or hollow organ wall 1, at one or both ends of the tubular implant 2. Thereafter, the locking element 86 is passed through the reinforcement ring 100, the anatomic vessel or hollow organ wall 1 and the tubular implant 2 so that the clamping element 88' is within the interior of the anatomic vessel or hollow organ wall 1. The locking element 86 is preferably passed through the reinforcement ring 100, the anatomic vessel or hollow organ wall 1 and the tubular implant 2 using a device of the type shown in FIGS. 5–7, 11, 19, 21 or 24, and in particular a hollow needle or trocar device with a sharp tip, which readily punches through reinforcement ring 100, the anatomic vessel or hollow organ wall 1 and the tubular implant 2. Once the clamping element 88' is located within the interior of the anatomic vessel or hollow organ wall 1 and the tubular implant 2, the retaining element 89' is pulled slightly outwardly, thereby seating the clamping element 88' against the tubular implant 2. Next, a tool, which may be of any type of conventional surgical grasping or clamping tool, is used to physically deform the portion of the retaining element 89' outside the anatomic vessel or hollow organ wall by bending the retaining element 89' down against the reinforcement ring 100. Thereafter, the tool may be disengaged from the retaining element 89'. In this manner, the retaining element 89' is clamped against the reinforcement ring 100 and the clamping element 88' is clamped against the tubular implant 2, thereby clamping the tubular implant 2 to the anatomic vessel or hollow organ wall 1.

Although in a preferred embodiment minimally-invasive techniques are used to insert and secure the locking elements into the hollow vessel or organ, it is to be understood that conventional open surgical techniques could also be used to open the area around the hollow organ or vessel and thereafter to secure the locking elements in place. For the repair of an AAA, for example, a laparotomy—through a markedly reduced midline incision $I_1$' above or near the umbilicus U, of, for example, 10 cm—would be performed and a self-retaining retractor would be used to displace the small bowel and transverse colon and gain access to the area of the aneurysm site.

Thus, there is shown and described a unique design and concept for attaching a stent to a vascular wall. It is to be understood that the present invention could be used in other applications, for example, attaching any implant to the wall of any vessel or hollow organ, and is not limited to aortic stents. While this description is directed to a particular embodiment, it is understood that those skilled in the art may conceive modifications and/or variations to the specific embodiments shown and described herein. Any such modifications or variations which fall within the purview of this description are intended to be included as part of the invention. It is understood that the description herein is intended to be illustrative only and is not intended to be limitative. Rather, the scope of the invention described herein is limited only by the claims.

What is claimed is:

1. A method for securing an implant at a site in an anatomic wall comprising:
   guiding the implant to the site;
   making a percutaneous incision near the site;
   providing a tool holding at least one locking element including a clamping element and a retaining element;
   inserting the tool through the percutaneous incision;
   puncturing the exterior of the anatomic wall and the implant with a cannula;
   ejecting the clamping element into an interior of the anatomic wall so that a portion of the retaining element is located outside of the anatomic wall; and
   physically deforming the portion of the retaining element to thereby clamp the implant to the anatomic wall.

2. The method of claim 1 further comprising:
   making a second percutaneous incision in the proximity of the anatomic wall; and wherein the act of guiding includes guiding through the second percutaneous incision and to the site.

3. The method of claim 2, wherein:
   the act of making a second percutaneous incision includes making an incision near a femoral artery.

4. The method of claimed 2, wherein:
   the act of making a second percutaneous incision includes making an incision near an iliac artery.

5. The method of claim 2, wherein:
   the act of making a second percutaneous incision includes making an incision near a distal end of an abdominal aorta.

6. The method of claim 1 wherein
   the act of guiding include guiding the implant using interventional techniques.

7. The method of claim 1, further comprising:
   pulling the locking element taut after the act of ejecting the clamping element into the interior of the anatomic wall.

8. The method of claim 1 wherein:
   the act of guiding the implant to the site includes guiding the implant to an anatomic vessel.

9. The method of claim 1 wherein:
   the act of guiding the implant to the site includes guiding the implant to a hollow organ.

10. The method of claim 1 further comprising:
    making an additional percutaneous incision; and
    inserting an endoscope through the additional percutaneous incision.

11. The method of claim 1 further comprising:
    making an additional percutaneous incision; and
    inserting at least one tool through the additional percutaneous incision.

12. The method of claim 1 wherein:
    the portion of the retaining element is deformed by bending.

13. The method of claim 1 wherein:
    the portion of the retaining element is deformed by wrapping the portion of the retaining element into a coil shape.

14. The method of claim 13 wherein:
    the portion of the retaining element is wrapped around a cylindrical tip of a tool.

15. The method of claim 1 further comprising:
    Placing a reinforcement ring around an exterior of the anatomic wall, and
    wherein the portion of the retaining element is deformed against the reinforcement ring.

16. Apparatus for attaching an implant to an anatomic wall, the apparatus comprising:
    an implant locking device having a clamping element for disposition against said implant and having a retaining element configured to extend through said anatomic wall and said implant to said clamping element, said retaining element being flexibly joined to said clamping element at a location which a is intermediate between opposite ends of said clamping element, said flexible joining enabling said clamping element to be turned into a substantially parallel relationship with said retaining element during penetration of said locking device into said anatomic wall and said implant and enabling turning of said clamping element into a substantially transverse relationship to said retaining element following said penetration, said clamping element and said retaining element are made of metallic wire, the metallic wire which forms said retaining element is bent 360° to form an end of the retaining element that is remote from said clamping element and wherein parallel portions of said metallic wire extend from said end of said retaining element to said clamping element, and a weld joining said parallel portions of said metallic wire at least at one location thereon.

17. In an implant and implant locking device for disposition at an anatomic wall, the combination comprising:
    a stent configured for emplacement at a first side of the anatomic wall, a body of cushioning material configured for emplacement at an opposite side of the anatomic wall, a clamping element extending within said stent, and a retaining element extending from said clamping element and which penetrates said stent and said body of cushioning material, said retaining element being connected to said clamping element at a location thereon which is intermediate between ends of the clamping element, said clamping element being turnable relative to said retaining element between a first orientation at which the clamping element extends in substantially parallel relationship with the retaining element and a second orientation at which the clamping element extends in a substantially transverse relationship with the retaining element and abuts an inner surface of said stent.

18. The apparatus of claim 17 wherein said clamping element and said retaining element are formed by an integral body of wire having arms which extend in part al relationship to from said retaining element and which are bent outward at said location to form said clamping element.

19. The apparatus of claim 17 wherein said clamping element is connected to said retaining element by a pivot connection at said location.

20. The apparatus of claim 17 wherein said stent has a curved inner surface and wherein said clamping element has a curvature substantially conforming with the curvature of said inner surface of said stent.

21. The apparatus of claim 17 wherein said retaining element is formed of bendable material and wherein a portion of the retaining element is bent to lay against said body of cushioning material to secure said retaining element and clamping element and said stent in place.

* * * * *